United States Patent
Baykal

(10) Patent No.: US 7,306,562 B1
(45) Date of Patent: Dec. 11, 2007

(54) MEDICAL RISK ASSESSMENT METHOD AND PROGRAM PRODUCT

(75) Inventor: Demir Baykal, Duluth, GA (US)

(73) Assignee: Medical Software, LLC, Atlanta, GA (US)

(*) Notice: Subject to any disclaimer, the term of this patent is extended or adjusted under 35 U.S.C. 154(b) by 345 days.

(21) Appl. No.: 10/831,481

(22) Filed: Apr. 23, 2004

(51) Int. Cl.
A61B 5/00 (2006.01)

(52) U.S. Cl. .................. 600/481; 600/300; 705/2

(58) Field of Classification Search ........... 600/300, 600/481
See application file for complete search history.

(56) References Cited

U.S. PATENT DOCUMENTS

| | | | |
|---|---|---|---|
| 5,396,886 A | 3/1995 | Cuypers | |
| 5,746,204 A | 5/1998 | Schauss | |
| 5,899,855 A | 5/1999 | Brown | |
| 5,965,449 A * | 10/1999 | Novak | 436/71 |
| 5,976,082 A | 11/1999 | Wong et al. | |
| 6,110,109 A | 8/2000 | Hu et al. | |
| 6,322,504 B1 * | 11/2001 | Kirshner | 600/300 |
| 6,421,650 B1 | 7/2002 | Goetz et al. | |
| 6,540,691 B1 * | 4/2003 | Phillips | 600/532 |
| 6,560,541 B1 | 5/2003 | Singh | |
| 6,576,471 B2 | 6/2003 | Otvos | |
| 6,602,469 B1 | 8/2003 | Maus et al. | |
| 2002/0056206 A1 * | 5/2002 | Pace et al. | 34/372 |
| 2002/0082906 A1 | 6/2002 | Kirshner | |
| 2002/0087276 A1 | 7/2002 | Otvos | |
| 2002/0095094 A1 | 7/2002 | Hutten et al. | |
| 2002/0123524 A1 | 9/2002 | Robins et al. | |
| 2002/0164598 A1 | 11/2002 | Muhlestein et al. | |
| 2002/0164662 A1 | 11/2002 | Hazen et al. | |
| 2003/0023387 A1 | 1/2003 | Gill-Garrison et al. | |
| 2003/0065241 A1 | 4/2003 | Hohnloser | |
| 2003/0119194 A1 | 6/2003 | Otvos | |
| 2003/0120134 A1 | 6/2003 | Rao et al. | |
| 2003/0182163 A1 | 9/2003 | Tice et al. | |
| 2003/0187688 A1 * | 10/2003 | Fey et al. | 705/2 |

(Continued)

OTHER PUBLICATIONS

P. Greenland, et al. Coronary Artery Calcium Score Combined With Framingham Risk Score for Risk Predition in Asymptomatic Individuals, JAMA, 2004; 209: 210-215.*

(Continued)

Primary Examiner—Charles A. Marmor, II
Assistant Examiner—Karen E Toth
(74) Attorney, Agent, or Firm—Womble Carlyle Sandridge & Rice, PLLC

(57) ABSTRACT

A medical risk assessment method and computer program product resident on a computer or a hand-held device that allows a physician to determine the best strategy for primary and secondary cardiovascular disease prevention utilizing current guidelines and published medical literature. The computer program product evaluates a number of risk factors to determine specific recommendations for an individual patient, including Framingham risk scoring (FRS), pertinent medical history, individual lipid panel and advanced lipoprotein profiling, patient laboratory test results, and published literature on the effects of anti-lipid medicines on plasma concentration and/or composition of lipoprotein molecules and clinical outcomes. The risk assessment method establishes a cardiovascular treatment therapy strategy for a patient by determining a cardiac risk classification group, determining a cardiovascular treatment therapy based on the patient's lipoprotein profile and the patient's cardiac group risk classification, and presenting the cardiovascular treatment therapy for the patient to a medical practitioner on a patient evaluation display.

33 Claims, 23 Drawing Sheets

U.S. PATENT DOCUMENTS

2005/0228692 A1* 10/2005 Hodgdon .................. 705/2
2005/0272054 A1* 12/2005 Cargill et al. .................. 435/6

OTHER PUBLICATIONS

M. Albert, et al. Plasma Concentration of C-Reactive Protein and the Calculated Framingham Coronary Heart Disease Risk Score, Circulation, 2003; 108; 161-165.*

Grundy et al. Assessment of Cardiovascular Risk by Use of Multiple-Risk-Factor Assessment Equations, Circulation, 1999; 100: 1481-1492.*

"Risk Assessment Tool for Estimating Your 10-Year risk of Having a Heart Attack"; http://hin.nhlbi.nih.gov/atpiii/calculator.asp?usertype=pub.

Gundy, et al.; AHA/ACC Scientific Statement: Assessment of Cardiovascular Risk by Use of Multi-Risk-Factor Assessment Equations; *Journal of American College of Cardiology Foundation*; 1999; 34: 1348-59.

"Lipids, Lipoproteins and Cardiovascular Risk Factors" topical search; *Clinical Chemistry*; http://www.clinchem.org/cgi/collection/LAL?page=16.

* cited by examiner

Group 1

Target: HDL < 130   and   LDL < 100
If CHD or SCD or PVD or DM or AAA is checked     }— 200

If TRG > 500
    FIBRATE & STATIN

=================== TRG less than 200 =========================

If TRG < 200 and LDL => 130

If (LDL * .53) > 100
        LIPITOR or CRESTOR

If (LDL * .65) > 100 and (LDL * .53) < 100 and (HDL * 1.13) < 40
        ADVICOR If (LDL * .65) > 100 and (LDL * .53) < 100 and
          (HDL * 1.07) < 40 and (HDL * 1.13) > 40
            ZOCOR
    else
        STATIN If (LDL * .65) < 100 and (HDL * 1.13) < 40
        ADVICOR If (LDL * .65) < 100 and (HDL * 1.07) < 40 and (HDL * 1.13) > 40
        ZOCOR
    Else
        STATIN

}— 210

If TRG < 200 and LDL < 100
    If HDL < 40
      If Cholesterol < 135
        NIASPAN If Cholesterol > 134
        NIASPAN If LPA > 20
        NIASPAN/ZOCOR

FIG. 2A

========= TRG greater than 200   And LDL Not Measured =============
If TRG > 200  And LDL = 0
    If NonHDL > 130
        If (HDL * 1.26) < 40
            If (CHOL * .67 - HDL * 1.3) > 130
                LIPITOR/CRESTOR
            Else
                ADVICOR If TRG > 200  And LDL = 0
    If NonHDL > 130
        If (HDL * 1.26) > 40  and (HDL * 1.19) < 40
            If (CHOL * .88 - HDL * 1.26) < 130
                NIASPAN
            If (CHOL * .67 - HDL * 1.30) > 130
                LIPITOR/CRESTOR
            Else
                ADVICOR If TRG > 200  And LDL = 0
    If NonHDL > 130
        If (HDL * 1.19) > 40  and (HDL * 1.07) < 40
            If (CHOL * .91 - HDL * 1.19) < 130
                FIBRATE
            If (CHOL * .88 - HDL * 1.26) < 130
                NIASPAN
            If (CHOL * .67 - HDL 1.30) > 130
                LIPITOR/CRESTOR
            Else
                ADVICOR If TRG > 200  And LDL = 0
    If NonHDL > 130
        If (HDL * 1.07) > 40
            If (CHOL * .88 - HDL * 1.26) >  130
                LIPITOR
            If (CHOL * .91 - HDL 1.19) > 130
                NIASPAN
            Else
                FIBRATE

```
If TRG > 200 And LDL = 0
    If NonHDL > 130
        If (HDL * 1.20) < 40
            NIASPAN
        Else
            FIBRATE
```
} 220

========== TRG greater than 200   And LDL Measured ===============

```
If  TRG >= 200 and LDL >= 130
    If (LDL * .55) > 100
        LIPITOR/CRESTOR
    If (HDL * 1.13) < 40 and (LDL * .55) < 100
        ADVICOR
        If (HDL * 1.13) > 40 and (LDL * .55) < 100
            If (HDL * 1.07) > 40
                If (HDL * 1.07) > 40
                    If (TRG * .75) > 200
                        LIPITOR,CRESTOR or ZOCOR
                    Else
                        ZOCOR 40

If  TRG > 200 and LDL > 100
    If HDL < 40
        If TRG < 300
            If * dCalcPercentLDL  > 100 and
               *dCalcPercentHDL  < 40
                ADVICOR
        Else
            NIASPAN
```

FIG. 2D

```
If  TRG > 200 and LDL > 100
    If HDL < 40
        If TRG > 300
            If (LDL * .83) <= 100 and (HDL * 1.13) <= 40
                NIASPAN
            If (LDL * .83) <= 100 and (HDL * 1.13) >= 40
                NIASPAN
            If (LDL * .83) > 100 and (HDL * 1.13) < 40
                ADVICOR
            If (LDL * .83) > 100 and (HDL * 1.13) > 40
                If (HDL * 1.07) < 40
```

} 230

```
                ZOCOR 40
            Else
                LIPITOR/CRESTOR

If  TRG > 200 and LDL > 100
    If HDL >= 40
        If (LDL * .83) > 100
            If (TRG * .65) > 200
                LIPITOR
        If (TRG * .75) > 200
            STATIN
        If (LDL * .83) < 100
            If LPA > 20
                NIASPAN
            If (TRG * .65) > 200
                LIPITOR/CRESTOR
            Else
                STATIN If  TRG > 200 and LDL < 100
    If HDL < 40
        If  *dCalcPercentLDL  <= 40 and
            (TRG * .65) < 200
                NIASPAN/FRIBRATE
        Else
            FIBRATE If  TRG > 200 and LDL < 100
    If HDL >= 40
        If NonHDL  <  130
            If Cholesterol > 135
                ZOCOR/CRESTOR
                If (TRG * .65) > 200
                    TRICOR/CRESTOR
                Else
                    NIASPAN
            If Cholesterol > 135
                ZOCOR
                If (TRG * .65) > 200
                    TRICOR
                Else
                    NIASPAN
```

Group 2

```
If TRG > 200 and LDL = 0 (Not measured)
    If (HDL * 1.20) < 40
        If (CHOL * .88 - HDL 1.26) < 160
            NIASPAN
        Else
            LIPITOR If TRG > 200 and LDL = 0 (Not measured)
    If (HDL * 1.20) >= 40
        If (CHOL * .88 - HDL 1.26) > 160
            LIPITOR
        If (CHOL * .91 - HDL * 1.19) < 160
            FIBRATE
        Else
            NIASPAN
```
⎱ 300

```
If TRG > 200 and LDL >= 160
    If *dCalcPercentLDL >= 160 and
        (LDL * .83) >= 160
            STATIN
    If HDL > 35
        STATIN
    If (HDL * 1.20) >= 35
        FIBRATE
    If (LDL * .83) <= 160
        NIASPAN
    else
        ADVICOR If TRG > 200 and LDL >= 130
    If HDL > 45
        If NonHDL > 190
            Re-Check
        Else
            DIET
    If HDL > 35
        STATIN
    If (HDL * 1.20) >= 35
        NIASPAN
    If *dCalcPercentLDL <= 130
        FIBRATE
    Else
```
⎱ 310

FIG. 3A

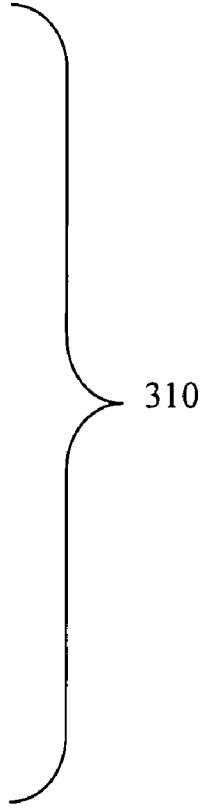
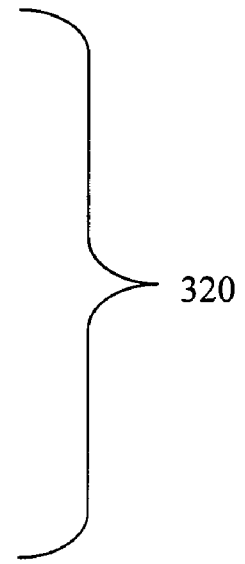
FIG. 3B

Group 3

Target: HDL < 160 and LDL < 130

If TRG > 200 and LDL = 0   (Not measured)
   If (HDL * 1.20) <= 40
      If (CHOL * .88 - HDL * 1.26) <= 160
         NIASPAN
     Else
        LIPITOR If TRG > 200 and LDL = 0   (Not measured)
   If (HDL * 1.20) > 40
      If (CHOL * .88 - HDL * 1.26) > 160
         LIPITOR
      If (CHOL * .91 - HDL * 1.19) <= 160
         FIBRATE
     else
        NIASPAN

} 400

============ LDL Measured ============================

If TRG > 200
    If LDL >= 130
       If (HDL * 1.07) >= 40
          STATIN
         If *dCalcPercentLDL >= 130 and
          ( LDL *.83) >= 130
            STATIN
         If *dCalcPercentLDL <= 130 and
          *dCalcPercentHDL >= 40
            FIBRATE
      Else
         If (LDL * .83) > 130
           ADVICOR
         Else
           NIASPAN

```
If LDL >= 100
    If NonHDL > 160
        If (HDL * 1.20) <= 40
            NIASPAN
        Else            (hdl * 1.20) > 40
            If *dCalcPercentLDL <= 130
                FIBRATE
            Else
                NIASPAN
    Else    (nonhdl < 160)
        DIET If LDL < 100
    If NonHDL <= 160
        DIET
    Else
        If HDL > 40
            DIET
        Else
            If (HDL * 1.20) <= 40
                NIASPAN
            Else
                If *dCalcPercentLDL <= 130
                    FIBRATE
                Else
                    NIASPAN
```
⎫
⎬ 410
⎭

============== TRG less than 200 ======================

```
If TRG < 200
    If LDL >= 130
        STATIN

If LDL < 100
        DIET  EXERCISE

If HDL < 40        (dead code)
        DIET    EXERCISE
    Else
        DIET & EXERCISE
```
⎫
⎬ 420
⎭

FIG. 4B

Group 4

Target: HDL < 190   and   LDL < 160
If one or none is check (SPB or Smoke or Family History or SAH)

If   TRG   >   500
    FIBRATE   &   NIASPAN

⎫ 500

================ TRG  >  200  and  LDL not Measured ============
If  TRG  >  200
   If   LDL  =  0
      If  (HDL * 1.20)  <=  40
         If ((Cholesterol * .88) - (HDL * 1.26)) <= 190
           NIASPAN
         Else
           LIPITOR
         If ((Cholesterol * .88) - (HDL * 1.26)) > 190
           LIPITOR
         If ((cholesterol * .91) - (HDL * 1.19)) <= 190
           FIBRATE
         Else
           NIASPAN

⎫ 510

================ TRG  >  200  and  LDL Measured ==============
If  TRG  >  200
   If LDL > 160
      If  (HDL * 1.07)  >=   40
         STATIN
      If  *dCalcPercentLDL  >=  160   and
        (LDL * .83)  >=  160
         STATIN
      If  *dCalcPercentLDL  <=  160   and
        *dCalcPercentHDL  >=  40
         FIBRATE
      If  (LDL * .83)  >=  160
         ADVICOR
      Else
         NIASPAN

```
If TRG > 200
    If LDL > 130
        If nonHDL >= 190
            If (HDL * 1.20) <= 40
                NIASPAN
            If *dCalcPercentLDL <= 160
                FIBRATE
            Else
                NIASPAN
If TRG > 200
    If LDL <= 130
        If NonHDL <= 190
            DIET
        If HDL >= 40
            DIET
        If (HDL * 1.20) <= 40
            NIASPAN
        If *dCalcPercentLDL <= 160
            FIBRATE
        Else
            NIASPAN
```
} 520

================== TRG < 200 and LDL Measured ============

```
If TRG < 200
    If LDL >= 160
        STATIN

If LDL <= 130
        DIET    STATIN
    If HDL <= 40
        DIET    EXERCISE
    Else
        DIET    EXERCISE
```
} 530

FIG. 5B

LDL

If TRG > 292 Then
  dMeanLDL = 726 - iTRG
  dResult = dMeanLDL * 0.103
  dCalcPercentLDL = (45# - dResult) / 100
    — 544

If TRG < 293 Then
  dMeanLDL = iTRG - 293
  dResult = dMeanLDL * 0.086
  dCalcPercentLDL = (31.5 + dResult) / 100
    — 548

540

HDL

If TRG > 432 Then
  dMeanHDL = 726 - iTRG
  dResultHDL = dMeanHDL * 0.011
  dCalcPercentHDL = (23# - dResultHDL) / 100
    — 554

If TRG < 433 Then
  dMeanHDL = iTRG - 432
  dResultHDL = dMeanHDL * 0.025
  dCalcPercentHDL = (19.6 + dResultHDL) / 100
    — 558

| Patient Evaluation |

AGE: |55|     NEW PATIENT ☑

STATIN: |0|▼   FIBRATE: |0|▼   NIASPAN: |0|▼   RESIN: |0|▼   ADVICOR: |0|▼

LIPITOR ☐   LESCOL ☐   TRICOR ☐           COLESTIPOL ☐
PRAVACHOL ☐   MEVACOR ☐   LOPID ☐       QUESTRAN ☐
ZOCOR ☐

┌─LABORATORY RESULTS─────────────────────────────┐
│ CHOLESTEROL |284|  SBP |122|  HDL |63|  LPa |0|  │
│ TRG |295|          LDL |162|  NON HDL 221        │
└──────────────────────────────────────────────────┘

CHD ☑   SCD ☐   PVD ☐   TYPE II DM ☐   AAA ☐
SBP ☐   SMOKE ☐   FAMILY ☐   SAH ☐
TREATED   Y/N   HISTORY

GUIDELINES RECOMMENDATION(S):
TARGET NON HDL-C < 130    TARGET LDL-C < 100
             STATIN

REFERENCE:

[COMPUTE]      [CLEAR]      [QUIT]

Patient Evaluation

AGE: 52    NEW PATIENT ☑ — 154

STATIN: 0 ▸   FIBRATE: 0 ▸   NIASPAN: 0 ▸   RESIN: 0 ▸   ADVICOR: 0 ▸ — 158

LIPITOR ☐   LESCOL ☐   TRICOR ☐         COLESTIPOL ☐
PRAVACHOL ☐ MEVACOR ☐  LOPID ☐          QUESTRAN ☐
ZOCOR ☐ — 162

LABORATORY RESULTS
CHOLESTEROL 239   SBP 152   HDL 41   LPa 0
TRG 527           LDL 133   NON HDL 198 — 166

CHD ☑    SCD ☐    PVD ☐    TYPE II DM ☐    AAA ☐ — 170
SBP ☐    SMOKE ☐  FAMILY ☐  SAH ☐
TREATED  Y/N      HISTORY — 174, 178, 182, 186

GUIDELINES RECOMMENDATION(S):
TARGET NON HDL-C < 130   TARGET LDL-C < 100 — 190

REFERENCE:                    FIBRATE   NIASPAN

COMPUTE    CLEAR              QUIT

Patient Evaluation

AGE: 75  NEW PATIENT ☑  FRS 15

STATIN: 0  FIBRATE: 0  NIASPAN: 0  RESIN: 0  ADVICOR: 0

LIPITOR ☐  LESCOL ☐  TRICOR ☐  COLESTIPOL ☐
PRAVACHOL ☐  MEVACOR ☐  LOPID ☐  QUESTRAN ☐
ZOCOR ☐

LABORATORY RESULTS

CHOLESTEROL 221  SBP 137  HDL 41  LPa 0

TRG 224  LDL 129  NON HDL 174

CHD ☐  SCD ☐  PVD ☐  TYPE II DM ☐  AAA ☐
SBP TREATED ☐  SMOKE Y/N ☐  FAMILY HISTORY ☐  SAH ☐

GUIDELINES RECOMMENDATION(S):

TARGET NON HDL-C < 190  TARGET LDL-C < 160

DIET

REFERENCE:

[COMPUTE]  [CLEAR]  [QUIT]

| Patient Evaluation | | |
|---|---|---|
| AGE: 30 | NEW PATIENT ☑ | FRS 0 |
| STATIN: 0 ▸ | FIBRATE: 0 ▸ | NIASPAN: 0 ▸ | RESIN: 0 ▸ | ADVICOR: 0 ▸ |

LIPITOR ☐   LESCOL ☐   TRICOR ☐   COLESTIPOL ☐
PRAVACHOL ☐ MEVACOR ☐  LOPID ☐    QUESTRAN ☐
ZOCOR ☐

LABORATORY RESULTS
COLESTEROL 227    SBP 130    HDL 46    LPa 0
TRG 57            LDL 170    NON HDL 181

CHD ☐      SCD ☐      PVD ☐      TYPE II DM ☐    AAA ☐
SBP ☐      SMOKE ☐    FAMILY ☐                    SAH ☐
TREATED    Y/N        HISTORY

GUIDELINES RECOMMENDATION(S):
TARGET NON HDL-C < 190    TARGET LDL-C < 160
                                STATIN
REFERENCE:

[COMPUTE]          [CLEAR]                    [QUIT]

Patient Evaluation

AGE: 75    NEW PATIENT ☑

STATIN: 0    FIBRATE: 0    NIASPAN: 0    RESIN: 0    ADVICOR: 0

LIPITOR ☐    LESCOL ☐    TRICOR ☐    COLESTIPOL ☐
PRAVACHOL ☐    MEVACOR ☐    LOPID ☐    QUESTRAN ☐
ZOCOR ☐

— LABORATORY RESULTS —
CHOLESTEROL 178    SBP 148    HDL 63    LPa 0
TRG 55    LDL 104    NON HDL 115

CHD ☑    SCD ☐    PVD ☐    TYPE II DM ☐    AAA ☐
SBP ☐    SMOKE ☐    FAMILY ☐    SAH ☐
TREATED    Y/N    HISTORY

GUIDELINES RECOMMENDATION(S):
TARGET NON HDL-C < 130    TARGET LDL-C < 100
STATIN
REFERENCE:

[ COMPUTE ]    [ CLEAR ]    [ QUIT ]

Patient Evaluation

AGE: 65    NEW PATIENT ☑    FRS 14

STATIN: 0 ▾   FIBRATE: 0 ▾   NIASPAN: 0 ▾   RESIN: 0 ▾   ADVICOR: 0 ▾

LIPITOR ☐   LESCOL ☐   TRICOR ☐   COLESTIPOL ☐
PRAVACHOL ☐   MEVACOR ☐   LOPID ☐   QUESTRAN ☐
ZOCOR ☐

LABORATORY RESULTS

CHOLESTEROL 217    SBP 130    HDL 54    LPa 0

TRG 232    LDL 117    NON HDL 163

CHD ☐   SCD ☐   PVD ☐   TYPE II DM ☐

SBP TREATED ☑   SMOKE Y/N ☐   FAMILY HISTORY ☐   SAH ☑   AAA ☐

GUIDELINES RECOMMENDATION(S):
TARGET NON HDL-C < 160    TARGET LDL-C < 130

NIASPAN

REFERENCE:

[ COMPUTE ]   [ CLEAR ]   [ QUIT ]

MEDICAL RISK ASSESSMENT METHOD AND PROGRAM PRODUCT

BACKGROUND OF THE INVENTION

The present invention relates generally to analysis of patient specific medical history and laboratory results, and more particularly to computer-implemented methods and products for assessing a patient's medical risks and formulating a treatment strategy.

Coronary heart disease is the leading cause of morbidity and mortality in the United States, accounting for approximately 500,000 deaths per year, and an associated annual morbidity cost of more than $200 billion. Over the past several decades, numerous clinical and epidemiological studies have shown that an elevated blood cholesterol level is one of the major modifiable risk factors associated with the development of coronary heart disease. These studies have demonstrated that low-density lipoprotein (LDL) cholesterol is a primary lipoprotein mediating atheroscelorsis. Cigarette smoking, hypertension, diabetes, and a low level of high-density lipoprotein (HDL) cholesterol are other risk factors that have been implicated in coronary heart disease.

The National Institutes of Health established the National Cholesterol Education program in 1985. The National Cholesterol Education Program Adult Treatment Panel I (NCEP-ATP I) developed its first set of guidelines in 1988. The guidelines establish clear goals for patients with lipid abnormalities. Revised guidelines were developed in 1993 (NCEP-ATP II) and in 2001 (NCEP-ATP III). Risk stratification continues to determine LDL goals and the intensity of LDL-lowering therapy. Dietary therapy remains the first line of treatment with drug therapy reserved for use in patents at high risk for coronary heart disease or patients who do not respond to non-pharmacological therapy.

Under the current guidelines, optimal cholesterol screening now includes a lipoprotein profile, preferably using blood drawn in a fasting state. The lipoprotein profile includes total cholesterol, LDL cholesterol, HDL cholesterol, and triglycerides. The lipoprotein profile cannot be interpreted without knowledge of the patient's risk factors. The major risk factors that modify low-density lipoprotein goals include age (men over 45, women over 55 having normal onset menopause), smoking status (current tobacco user or within the last 5 years), hypertension (blood pressure exceeding 140/90 mmHg), high-density lipoprotein levels, and family history of coronary artery disease. Patients with diabetes and those with a ten year cardiac event risk of 20% or greater are considered coronary heart disease equivalents. An additional step in the determination of coronary heart disease risk involves the calculation of the Framingham risk score (FRS) for persons with two or more risk factors. The ATP III Guidelines also raise the threshold of low HDL cholesterol from less than 35 mg/dL to less than 40 mg/dL. An HDL level of 60 mg/dL or higher is considered to be a negative risk factor.

The FRS is a risk assessment tool that has been derived from data collected in the Framingham heart study. The ATP III Guidelines recommend that patients with two or more risk factors have their FRS calculated. The FRS consist of points that are allocated based on various degrees of risk associated with five categories: age, total cholesterol level, HDL cholesterol level, tobacco smoking status and hypertension and whether this condition is treated. The FRS point total results in a percent risk of having a cardiac event in the next ten years.

In the ATP III Guidelines, the target LDL level for patients with established coronary heart disease is still 100 mg/dL or less. Patients with diabetes and patients with an FRS of 20% or higher are considered coronary heart disease equivalents. Since patients with diabetes and patients with an FRS of 20% or higher are in the same risk category as coronary heart disease patients, it is recommended that they maintain an LDL level of 100 mg/dL.

The extent of LDL lowering therapy depends on the patient's coronary heart disease risk. The two major modalities for lowing the LDL level advocated by the ATP III Guidelines are therapeutic lifestyle changes and drug therapy. Patients are classified in one of three categories of risk: (1) coronary heart disease (CHD) and CHD equivalents, (2) two or more risk factors, or (3) zero or one risk factors. The two or more risk factors category can be further subdivided into patients having an FRS score 12 or higher and patients having an FRS score less than 12.

Therapeutic lifestyle changes encompass diet, physical activity and weight loss. The ATP III Guidelines continue to stress the importance of non-pharmacological treatment, but recognize its limitations by reducing the trial of these modalities from six months to twelve weeks before considering the use of medications to assist in achieving recommended LDL goals.

The failure of therapeutic lifestyle changes to modify LDL cholesterol levels or the presence of high CHD risk levels warrants the use of drug therapy. Several drugs have specific effects on lipoprotein metabolism, including bile acid sequestrants (resins), fibric acids, nicotinic acid, and statins. Bile acid sequestrants include cholestyramine, colestipol, and colesevelam. Fibric acids include gemfibrozil and fenofibrate. Nicotinic acid includes extended-release nicotinic acid (Niaspan) and sustained release nicotinic acids. The statins include lovastatin (Levitor), pravastatin (Pravachol), fluvastatin (Lescol), atorvastatin (Mevacor), synvastatin (Zorcor) and rosuvastatin (Crestor). If the LDL goal based on established risk is not achieved, therapy should be intensified with an increase in drug dosage or the addition of another LDL-lowering drug.

The ATP III Guidelines recognized the increasing number of studies correlating elevated triglyceride levels with increased coronary artery disease risk. The ATP III Guidelines lowered the acceptable triglyceride level from the ATP II Guidelines. The primary modes of treating hypertriglyceridemia are diet and exercise. If indicated, nicotinic acid and fibric acid derivatives are the most effective drugs in lowering triglyceride levels. Triglyceride reduction is also a secondary benefit of statins.

Niapsan is one of only two products in the United States approved for increasing HDL levels. Low HDL cholesterol levels have been shown to be one of the highest risk factors contributing to coronary heart disease. Most of the drugs for treating cholesterol problems are designed to reduce LDL levels. Niaspan's active ingredient, niacin, is most effective in elevating HDL levels. The increase in HDL has been shown to significantly reduce the chances of coronary heart disease.

Statins work by slowing down the liver's production of cholesterol, high levels of which are implicated in atheroschelorsis, a disease process that leads to clogging of the arteries. Heart attack patients typically are given one of the FDA-approved statins at the time of discharge or within months of discharge from the hospital as a preventative measure against future heart attacks. Because of their effectiveness as a class for reducing LDL cholesterol and their favorable safety profile, statins are by far the most frequently used drugs as first line therapy for patients with high LDL cholesterol. Statins generally raise HDL cholesterol levels and lower plasmatriglycerides.

Three bile acid-binding sequestrants are currently available in the United States: cholestyramine (Questran), colestipol (Colestid), and colesevelan hydrochloride (Welchol). These resins significantly decrease LDL cholesterol and can produce small increases in HDL cholesterol. Bile acid sequestrants should generally not be used in patients with triglyceride levels above 200 mg/dL, and should not even be considered for use in patients with triglyceride levels exceeding 400 mg/dL.

Fibrates that are currently available in the United States include gemfibrozil (Lopid) and fenofibrate (TriCor). Gemfibrozil and fenofibrate can decrease triglyceride levels, increase HDL cholesterol levels and shift small, dense LDL particles toward larger, more buoyant sizes, improving and potentially correcting the lipoprotein abnormalities commonly found in Type II diabetes. Since neither fibrate drug adversely affects glycemic control, either can by used in patients with diabetes.

There is a need for a computer-implemented method and computer program product that can enable a physician to quickly assimilate all the pertinent medical data and guidelines recommendations necessary to evaluate a patient's medical risk for cardiovascular disease and determine a patient care management program that is best suited for an individual patient.

SUMMARY OF THE INVENTION

The present invention is a medical risk assessment method and computer program product that is resident on a computer or a hand-held device and that allows a physician to determine the best strategy for primary and secondary cardiovascular disease prevention utilizing current guidelines and published medical literature. The computer software program evaluates a number of risk factors to determine specific recommendations for an individual patient, including Framingham risk scoring (FRS), pertinent medical history, individual lipid panel and advanced lipoprotein profiling, patient laboratory test results, and published literature on the effects of anti-lipid medicines on plasma concentration and/or composition of lipoprotein molecules and clinical outcomes.

In one exemplary embodiment of the invention, a computer-implemented risk assessment method establishes a cardiovascular treatment therapy strategy for a patient by determining a cardiac risk classification group for the patient based on a predetermined set of cardiac risk factors, determining a cardiovascular treatment therapy based on the patient's lipoprotein profile and the patient's cardiac group risk classification; and presenting the cardiovascular treatment therapy for the patient to a medical practitioner on a patient evaluation display.

BRIEF DESCRIPTION OF THE DRAWINGS

The invention is better understood by reading the following detailed description of the invention in conjunction with the accompanying drawings, wherein:

FIGS. 2A–2E illustrates the Group 1 processing logic of the medical risk assessment software in accordance with an exemplary embodiment of the present invention.

FIGS. 3A–3B illustrate the Group 2 processing logic of the medical risk assessment software in accordance with an exemplary embodiment of the present invention.

FIGS. 4A–4B illustrate the Group 3 processing logic of the medical risk assessment software in accordance with an exemplary embodiment of the present invention.

FIGS. 5A–5B illustrate the Group 4 processing logic of the medical risk assessment software in accordance with an exemplary embodiment of the present invention.

FIG. 5C illustrates the LDL reducing and HDL reducing power algorithms included in the Groups 1–4 processing logic of the medical risk assessment software.

FIGS. 6–15 illustrate displays of sample results including specific patient therapy recommendations derived from use of the medical risk assessment software in accordance with an exemplary embodiment of the present invention.

DETAILED DESCRIPTION OF THE INVENTION

Figure 1:
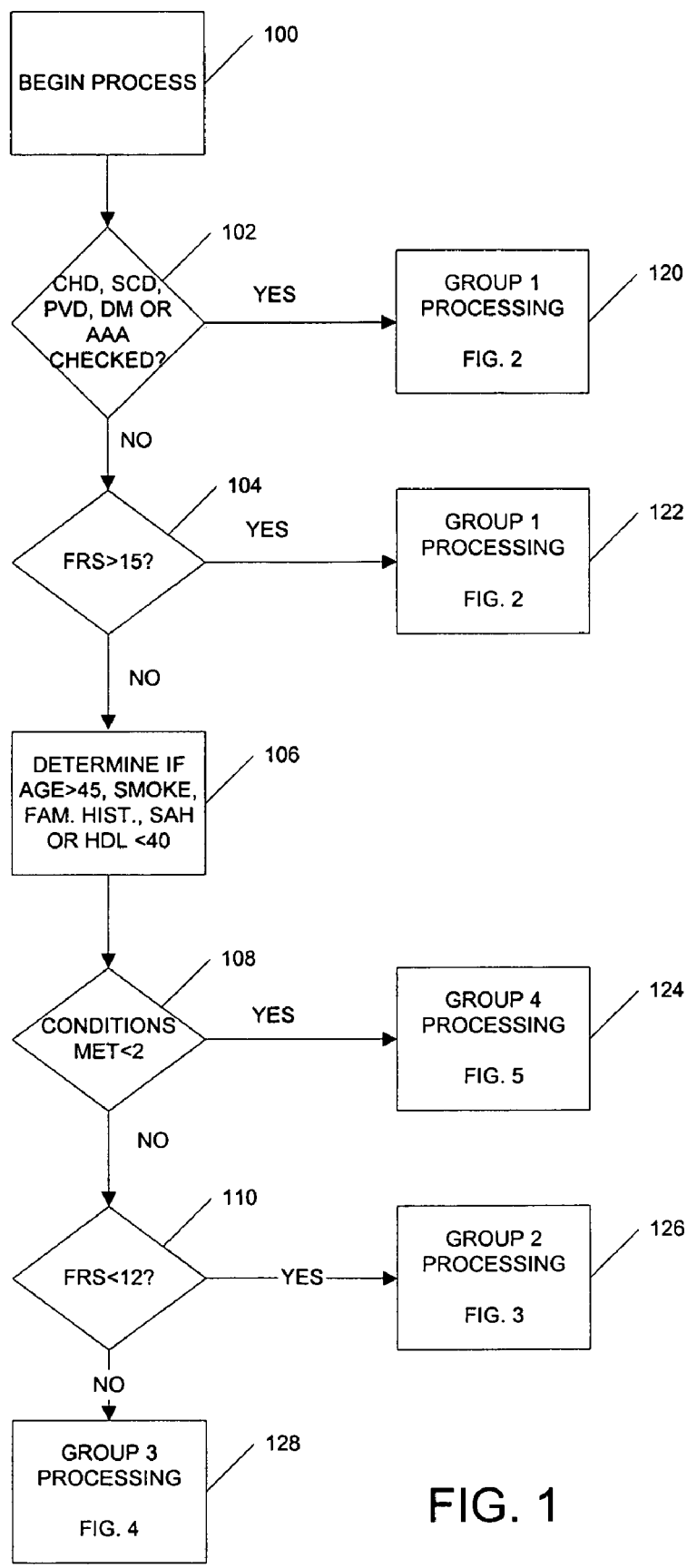
FIG. 1 illustrates the high level processing logic of the medical risk assessment software in accordance with an exemplary embodiment of the present invention.

The following description of the present invention is provided as an enabling teaching of the invention in its best, currently known embodiment. Those skilled in the relevant art will recognize that many changes can be made to the embodiment described, while still obtaining the beneficial results of the present invention. It will also be apparent that some of the desired benefits of the present invention can be obtained by selecting some of the features of the present invention without using other features. Accordingly, those who work in the art will recognize that many modifications and adaptations to the present invention are possible, and may even be desirable in certain circumstances, and are a part of the present invention. Thus, the following description is provided as illustrative of the principles of the present invention and not in limitation thereof, since the scope of the present invention is defined by the claims.

The medical risk assessment software and method of the invention allows a physician to establish an accurate strategy for primary and secondary cardiovascular disease prevention utilizing current guidelines and published medical literature. The software includes artificial intelligence for making clinical decisions in specific situations. The medical risk assessment software takes into consideration a number of key factors including Framingham risk scoring, pertinent medical history, individual lipid panel and advanced lipoprotein profiling, and pertinent individual laboratory values such as serum creatine glucose. Pertinent medical history includes existing conditions such as coronary heart disease (CHD), symptomatic carotid disease (SCD), peripheral vascular disease (PVD), Type II Diabetes Mellitus (Type II DM), abdominal aortic aneurysm (AAA), systolic blood pressure (SPB) treatment, systolic arterial hypertension (SAH), family history of premature coronary artery disease, and whether the patient is a smoker. Individual lipid panel and advanced lipoprotein panel includes cholesterol, systolic blood pressure, triglycerides, high density lipoproteins (HDL), low density lipoprotein (LDL), and non-HDL. The medical risk assessment software also takes into consideration the effects of currently available anti-lipid medicines on plasma concentration and/or composition of lipoprotein molecules and clinical outcomes as published in medical literature. The medical risk assessment software makes specific management recommendations for individuals, with or without existing cardiovascular conditions, integrating their clinical and laboratory profiles with results in current published literature and displaying all of this pertinent information and recommended treatment therapies on a patient evaluation display.

The present invention can be implemented on a general purpose computer, a computer network, an Internet-based system, a personal digital assistant (PDA) or as an embedded system. The present invention can be implemented as a portable product to operate on a personal computer, a computer workstation or a mainframe computer. The computer utilized can be of conventional design, having a processing unit, an input device, an output device, and a memory unit interconnected by a communications bus. The memory unit can be a conventional random-access memory (RAM) and a hard disk drive. The memory unit stores a plurality of databases and a plurality of computer instructions that implement the methods and program products of the invention. Two databases are used to implement the invention in one exemplary embodiment. The first contains data extracted from published medical guidelines such as the ATP III guidelines. The second contains data extracted from published medical literature that documents the effects of anti-lipid medicines. In an alternative embodiment, these databases can be integrated to form a single database. The computer program instructions may be implemented in various computer programming languages such as C, C++, Java and can incorporate extracted guidelines and extracted test results into processing algorithms. The program instructions provide the processing logic to evaluate patient-specific information to determine cardiovascular treatment recommendations to display to the physician.

The high level processing logic for the medical risk assessment software is illustrated in FIG. 1. After the medical risk assessment process is initiated in logic block 100, a test is made in decision block 102 to determine if the patient has any existing CHD, SCD, PPD, DM or AAA condition checked. If the patient has any of these conditions, then Group 1 processing is performed as indicated in logic block 120. Group 1 processing logic is shown in FIGS. 2A–2E. If the patient does not have any of the conditions tested for in decision block 102, then in decision block 104, a test is made to determine if the patient has a Framingham risk score greater than 15. If the patient has an FRS>15, then Group 1 processing is performed as indicated in logic block 122. If the patient has an FRS≦15, then a determination is made if the patient's age is greater than 45, whether the patient smokes, has a pertinent family history of coronary artery disease (CAD), has systolic arterial hypertension, or an HDL less than 40. A test is then made in decision block 108 to determine if the number of conditions met is less than 2. If it is, then Group 4 processing is performed as indicated in logic block 124. In decision block 108, if two or more conditions are met, a test is then made in decision block 110 to determine if the Framingham risk score is less than 12. If the FRS is less than 12, then Group 2 processing is performed as indicated in logic block 126. If FRS is 12 or higher, then Group 3 processing is performed as indicated in logic block 128.

Figure 2B:
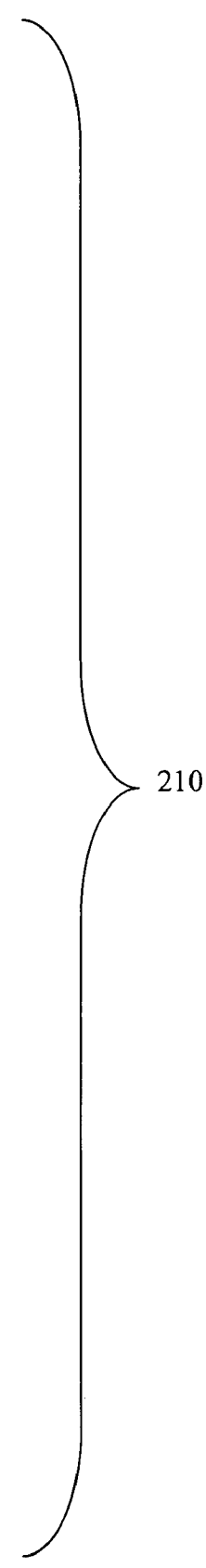

FIGS. 2A–2E illustrate the Group 1 processing logic of the medical risk assessment software. For Group 1 patients, the target HDL level is less than 130, and the target LDL level is less than 100. If the patient has a history of CHD, SCD, PPD, DM or AAA, or if the patient has a Framingham risk score exceeding 15, then the processing logic in FIGS. 2A–2E is executed to provide recommended treatment therapies for the patient. The processing logic is divided into four sections: 200, 210, 220, and 230. If the patient has a triglycerides (TRG) level that is greater than 500, then processing logic section 200 is performed (FIG. 2A). In this case, the recommendation would be to prescribe a fibrate and a statin. If the patient's TRG level is less than 200, processing logic 210 is performed (FIGS. 2A–2B). The medical risk assessment software provides a patient therapy recommendation to the physician based on the patient's TRG, LDL, and HDL levels. If the TRG level is greater than 200, but the LDL is not measured, processing logic section 220 is performed as illustrated in FIG. 2C. An LDL equal to zero in the processing logic code means that the LDL level is not measured. The recommended patient therapy in FIG. 2C is based upon non-HDL level, HDL level, and total cholesterol level. Based on the total cholesterol level, the HDL level and the non-HDL level, a specific drug is recommended for patient therapy such as Lipitor, Advicor, Niaspan, or a fibrate. Advicor is a combination product containing both extended-release niacin and lovastatin. This drug has been approved for the treatment of primary hypercholesterolemia dyslypidemia. Advicor is indicated for patients who were previously treated with either of its component, but who require additional lipid modification for LDL or HDL cholesterol and triglycerides. Advicor lowers total cholesterol and LDL cholesterol, while raising the amount of HDL cholesterol.

FIGS. 2D–2E illustrate the processing logic performed when the Group 1 patient's TRG is greater than 200 and the patient's LDL level is measured. The patient therapy recommendations provided by the processing logic section 230 are based on TRG level, LDL level, non-HDL level, and Lipoprotein (a) (LPA) level.

Group 2 processing is illustrated in FIGS. 3A–3B. The Group 2 patient category is for those patients without a history of CHD, SCD, PPD, DM or AAA, meeting two or more of the conditions shown in logic block 106 of FIG. 1, but having a Framingham risk score less than 12. The conditions that are determined in logic block 106 of FIG. 1 are whether the patient's age is greater than 45, whether the patient smokes, whether the patient has a history of systolic arterial hypertension, whether the patient's HDL level is less than 40, and the patient's family history of CAD. The processing logic in FIGS. 3A–3B are divided into three sections: 300, 310, and 320. The processing logic section 300 is performed if the patient's triglycerides level exceeds 200 and the patient's LDL level is not measured. Processing logic section 310 is performed if the patient's TRG level exceeds 200 and the patient's LDL level is measured. Logic processing section 320 is performed if the patient's TRG level is less than 200. In processing logic 300, TRG, HDL and cholesterol levels are used to determine a treatment therapy for the patient. In processing logic 310, TRG, LDL, and non-HDL levels are used to determine a recommended patient treatment therapy. In processing logic 320, TRG, LDL and HDL levels are used to determine a recommended treatment therapy for the patient.

FIGS. 4A–4B illustrate the Group 3 processing logic. Patients in Group 3 are those without a history of CHD, SCD, PPD, DM, or AAA, meeting more than two conditions in logic block 106 of FIG. 1 and having a Framingham risk score greater than or equal to 12. The target HDL is less than 160 and the target LDL is less than 130 for patients in Group 3. Group 3 processing logic is divided into processing logic sections 400, 410, and 420. Processing logic section 400 is performed if the patient's TRG level exceeds 200 and the patient's LDL level is not measured. This processing logic uses TRG level, HDL level and total cholesterol level to determine a recommended treatment therapy for the patient. Processing logic section 410 is performed if the patient's TRG level exceeds 200 and the patient's LDL level is measured. The patient's TRG, LDL, HDL and non-HDL levels are used to determine a recommended treatment therapy. Processing logic section 420 is performed if the patient's TRG level is less than 200. The patient's TRG, LDL, and HDL levels are taken into consideration in determining a recommended treatment therapy.

Group 4 processing logic is illustrated in FIGS. 5A–5B. Group 4 processing logic is executed if the patient has no history of CHD, SCD, PPD, DM, or AAA, and has either none or one of the conditions listed in logic block 106 of FIG. 1. For Group 4 patients, the target HDL level is less than 190 and the target LDL level is less than 160. Group 4 processing logic is divided into sections 500, 510, 520, and 530. If the patient's TRG level exceeds 500, then the recommended therapy is to prescribe a fibrate and Niaspan as illustrated in processing logic section 500. If the patient's TRG exceeds 200, but the LDL is not measured, then processing logic section 510 is performed. TRG, total cholesterol and HDL levels are used to determine a recommended treatment therapy for the patient. If the patient's TRG level exceeds 200 and LDL is measured, then processing logic section 520 is performed. A recommended treatment therapy is determined based on the patient's TRG level, LDL level, non-HDL level and HDL level. If the patient's TRG level is less than 200 and LDL is measured, then processing logic section 530 is performed. The patient's TRG level, LDL level and HDL level are used to determine a recommended treatment therapy.

FIG. 5C illustrates the LDL reducing and HDL reducing power algorithm included in the Groups 1–4 processing logic of the medical risk assessment software. The reducing power algorithms are performed when the patient's TRG level exceeds 200 and the patient's LDL is measured. The reducing power algorithms are divided into sections 540 and 550. The LDL reducing power algorithm section 540 is further subdivided into subsection 544 for TRG greater than 292 and subsection 548 for TRG less than 293. The HDL reducing power algorithm section 550 is further subdivided into subsection 554 for TRG greater than 432 and subsection 558 for TRG less than 433. The LDL and HDL reducing power algorithm are for use in processing logic sections 230, 310, 410 and 520 of FIGS. 2–5, respectively.

Patient evaluation display examples are provided in FIGS. 6–15. The patient evaluation display is divided into a number of sections. Section 154 enables entry of the patient's age, whether the patient is a new patient, and where calculated, a Framingham risk score. Section 158 lists current patient therapies. A "0" indicates that the patient is not receiving the particular therapy. A "1" indicates that the patient is receiving the corresponding therapy. Section 162 is used to identify specific drugs that the patient may currently be using, including a specific statin, fibrate, or resin. Laboratory results for the patient are entered in section 166. Laboratory results include total cholesterol level, systolic blood pressure, HDL level, LPA level, triglycerides level, and LDL level. The non-HDL level is determined by subtracting the HDL level from the total cholesterol level. Sections 170 and 174 indicate the patient's pertinent medical history. Section 170, in particular, lists the five key risk factors, i.e., CHD, SCD, PVD, Type II DM, and AAA, that will classify the patient in Group 1 for processing by the medical risk assessment software. Section 174 lists the risk factors that are used to determine whether the patient should be classified in Group 2, Group 3, or Group 4 for processing by the medical risk assessment software. The guidelines recommendations are listed in Section 178 and are based on the patient's laboratory results and pertinent medical history. Section 182 displays the recommended patient therapy that is determined on the basis of the underlying processing logic that is performed based on the patient's age, laboratory results, key risk factors, and other risk factors. Section 186 is a reference section that provides a reference to specific published literature where appropriate. Section 190 of the patient evaluation display contains three selectable buttons to (1) compute a recommended patient treatment therapy, (2) clear the screen, or (3) quit the medical risk assessment software program.

In the example of FIG. 6, the patient is 55 years old and has a TRG of 295, an LDL of 162 and an HDL of 63. There is an indication in section 170 that the patient has a CHD condition. Corresponding to decision block 102 in FIG. 1, this results in the patient being classified in Group 1 and the processing logic of FIGS. 2A–2E being executed. The guideline recommendations for this specific patient are a target non-HDL cholesterol level less than 130 and a target LDL cholesterol less than 100. Since the patient has a TRG level greater than 200, and a measured LDL level, the processing logic section 230 will be performed by the medical risk assessment software to determine the recommended treatment therapy. For this patient, the recommended treatment therapy is a statin as indicated in section 182 of FIG. 6.

Figure 7:
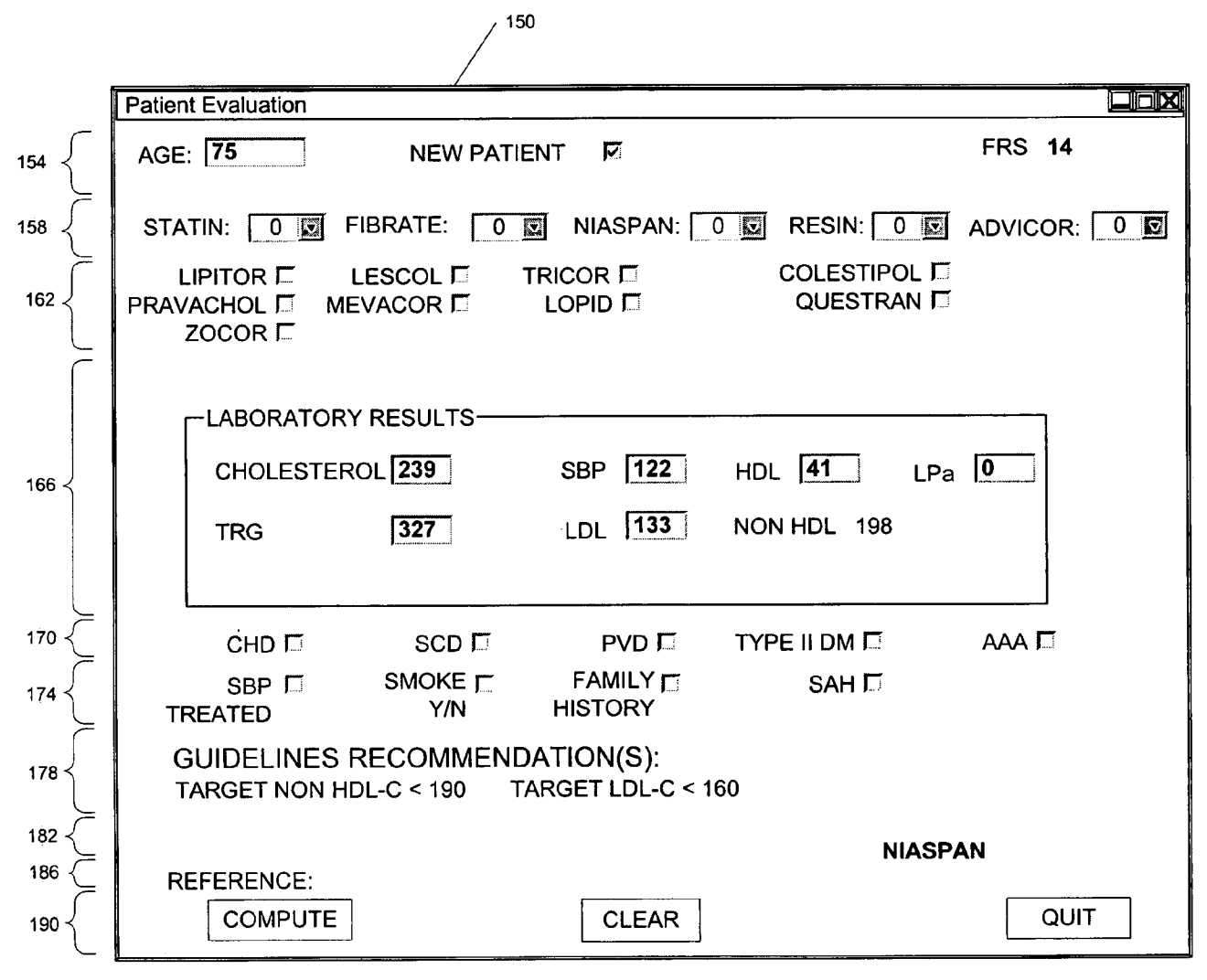

In the example of FIG. 7, the patient is 75 years old and has a TRG of 327, an LDL of 133 and an HDL of 41. Non of the high risk factors in section 170 are checked. The FRS is computed for the patient and is determined to be less than 15. This leads to a determination in logic block 106 whether one or more of the conditions of age, smoking, family history, SAH, or HDL less than 40, are met. None of the conditions in section 174 are checked, however, the patient is older than 45 as indicated in section 154. Since the number of conditions met is less than 2, the patient is classified in Group 4 and the processing logic section of FIGS. 5A–5B is performed. The guideline recommendations for this specific patient are a target non-HDL cholesterol level less than 190 and a target LDL cholesterol less than 160. Since the patient's TRG level exceeds 200 and the LDL is measured, processing logic section 520 is performed to determine the recommended patient therapy. In this example, the recommended patient therapy is Niaspan as indicated in Section 182.

In the example of FIG. 8, the patient is 52 years old and has a TRG of 527, and LDL of 133 and an HDL of 41. The CHD risk factor is checked in section 170, therefore the patient is classified in Group 1 and the processing logic of FIGS. 2A–2E is executed. The guideline recommendations for this specific patient are a target non-HDL cholesterol level less than 130 and a target LDL cholesterol less than 100. Since the patient has a TRG level greater than 500, processing logic section 200 is performed to determine the recommended patient therapy. Section 182 indicates to the physician the recommended patient therapy.

Figure 9:
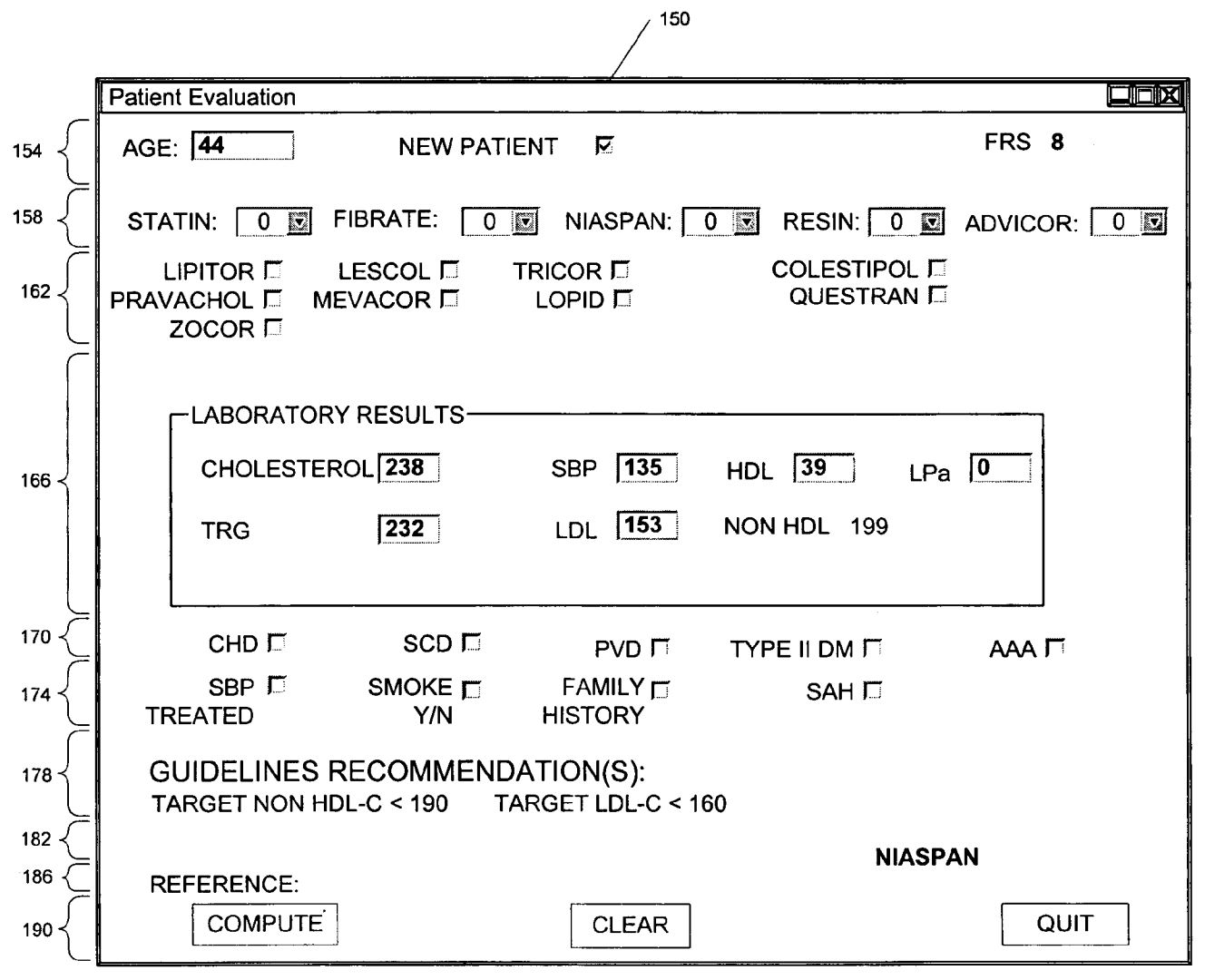

In the example shown in FIG. 9, the patient is 44 years old and has a TRG of 232, an LDL of 153 and an HDL of 39. The patient does not have any of the key risk factors in section 170 checked. Therefore the Framingham risk score is determined and is less than 15. The number of risk factor conditions is then determined as listed in logic block 106 of FIG. 1. Since none of the conditions in section 174 are checked and the patient's age is less than 45, the patient is classified in Group 4. The processing logic of FIGS. 5A–5B is then executed to determine a recommended patient therapy. The guideline recommendations for this specific patient are a target non-HDL cholesterol level less than 190 and a target LDL cholesterol less than 160. In this example, the TRG level exceeds 200 and the LDL level is measured. Therefore, processing logic section 520 is performed to determine the recommended treatment therapy displayed in section 182.

Figure 10:
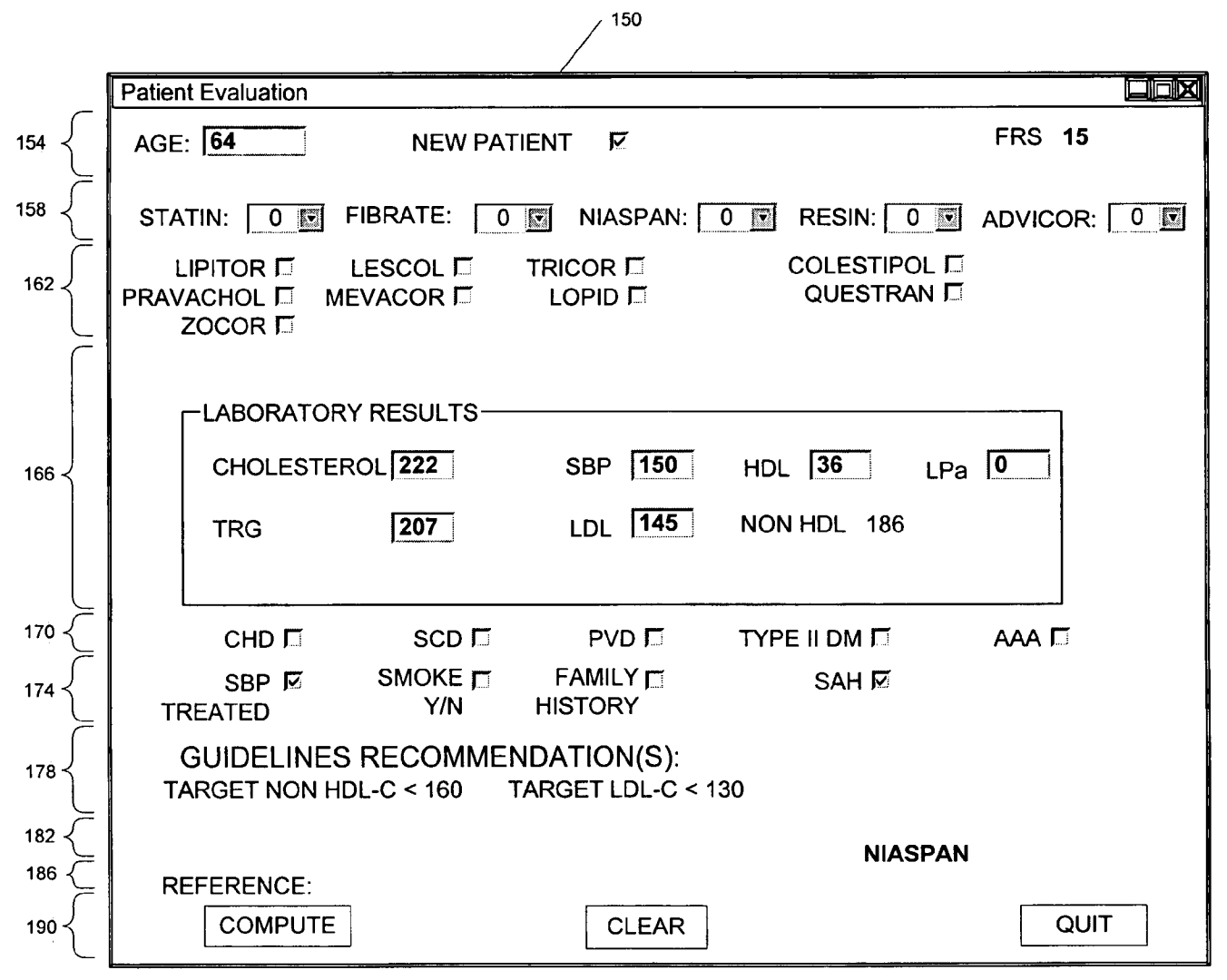

In the example shown in FIG. 10, the patient is 64 years old and has a TRG of 207, an LDL of 145 and an HDL of 36. None of the key risk factors in section 170 are checked; therefore, the Framingham risk score for the patient is determined. Since the patient's FRS score is not greater than 15, the patient's age and the number of other risk factors checked in section 174 are used to determine the patient's group classification. The number of conditions met is 3 in this example. Since the patient's FRS score is greater than 12, the patient is classified in Group 3 and the processing logic of FIG. 4 is executed. The guideline recommendations for this specific patient are a target non-HDL cholesterol level less than 160 and a target LDL cholesterol less than 130. The patient's TRG level exceeds 200, therefore, processing logic section 410 is performed to determine the recommended patient therapy. The medical risk assessment software determines that the recommended patient therapy is Niaspan as indicated in section 182.

In the example shown in FIG. 11, the patient is 75 years old and has a TRG of 224, an LDL of 129, and an HDL of 41. None of the high risk factors in section 170 are checked and the FRS score is not greater than 15. Therefore, the conditions listed in logic block 106 of FIG. 1 are determined for the patient. The only condition met is that the patient's age is greater than 45, therefore the patient is classified in Group 4 and the processing logic of FIGS. 5A–5B is executed. The guideline recommendations for this specific patient are a target non-HDL cholesterol level less than 190 and a target LDL cholesterol less than 160. Since the patient's TRG level exceeds 200, processing logic section 520 is performed. In this example, the patient's HDL exceeds 40, but the LDL level is less than 130. Therefore, the recommended patient therapy is determined to be diet, as indicated in section 182.

Figure 12:
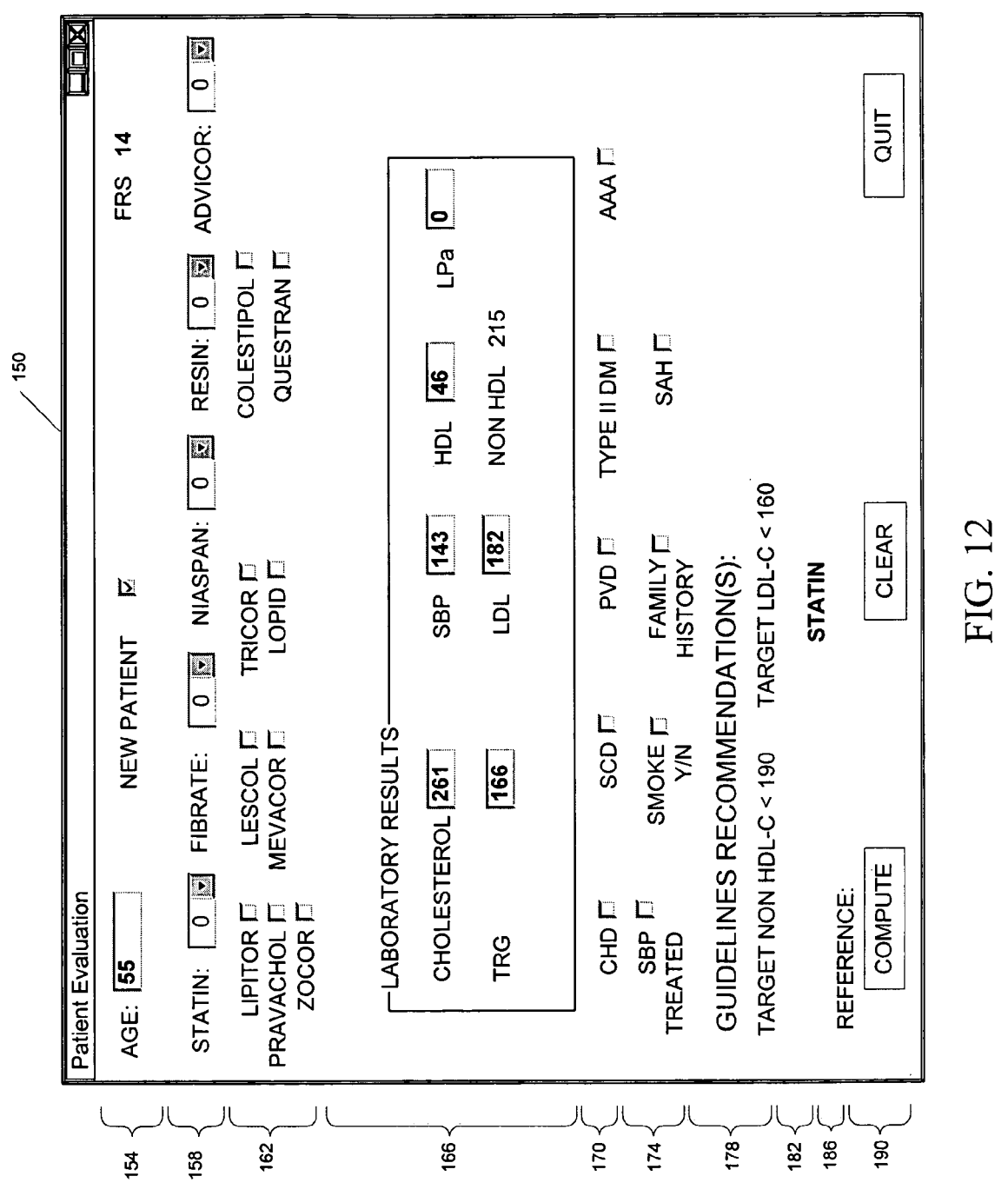

In the example shown in FIG. 12, the patient is 55 years old and has a TRG of 166, an LDL of 182 and an HDL of 46. None of the key risk factors in section 170 are checked and the FRS score is less than 15; therefore a determination is made of the number of conditions met by the patient that are listed in logic block 106 of FIG. 1. Since none of the conditions in section 174 are checked, and the patient's age exceeds 45, the patient is classified into Group 4 and the processing logic of FIGS. 5A–5B is executed. The guideline recommendations for this specific patient are a target non-HDL cholesterol level less than 190 and a target LDL cholesterol less than 160. In this example, the TRG level is less than 200 and the LDL level is measured; therefore processing logic section 530 is performed. For this patient, the LDL level exceeds 160, but the HDL level is greater than 45. Since the FRS score is greater than 12, the medical risk assessment software determines that the patient's treatment therapy should be a statin.

In the example shown in FIG. 13, the patient is 30 years old and has a TRG of 57, an LDL of 170, and an HDL of 46. None of the key risk factors are checked in section 170 and the Framingham risk score is 0 for this patient. Since none of the key risk factors were checked, and the FRS score is less than 15, the conditions listed in logic block 106 of FIG. 1 are examined to determine how many of the conditions are met. Since the patient's age is less than 45 and none of the conditions in section 174 are checked, the patient is classified in Group 4 and processing logic in FIGS. 5A–5B is executed. The guideline recommendations for this specific patient are a target non-HDL cholesterol level less than 190 and a target LDL cholesterol less than 160. This patient has a TRG level less than 200 and a measured LDL level, therefore, processing logic section 530 is performed to determine a recommended treatment therapy for the patient. The recommended treatment therapy is shown in section 182.

In the example shown in FIG. 14, the patient is 65 years old and has a TRG of 232, an LDL of 117, and an HDL of 54. CHD is checked in section 170. Since the patient has a key risk factor checked, the patient is classified in Group 1 and the processing logic of FIGS. 2A–2E is executed. The guideline recommendations for this specific patient are a target non-HDL cholesterol level less than 130 and a target LDL cholesterol less than 100. Since the patient has a TRG level less than 200 and a measured LDL level, processing logic section 210 is performed. The recommended patient treatment therapy is indicated in section 182.

In the example shown in FIG. 15, the patient is 65 years old and has a TRG of 232, an LDL of 117 and an HDL of 54. The patient does not have any of the key risk factors checked in section 170. The Framingham risk score for this patient is 14. Since none of the key risk factors are checked and the FRS score is less than 15, the number of conditions met by the patient that are listed in logic block 106 of FIG. 1 is determined to classify the patient. Since the patient's age is greater than 45 and two additional conditions are checked in section 174, the Framingham risk score is used to determine whether the patient is classified in Group 2 or in Group 3. In this instance, since the FRS is greater than 12, the patient is classified in Group 3. The processing logic of FIGS. 4A–4B is executed. The guideline recommendations for this specific patient are a target non-HDL cholesterol level less than 160 and a target LDL cholesterol less than 130. Since the patient's TRG level is greater than 200 and the patient's LDL level is measured, processing logic section 410 is performed to determine a recommended treatment therapy. In this example, the recommended treatment therapy is Niaspan, as indicated in section 182.

It is important to note that the present invention has been described in the context of a fully functioning data processing system, although those skilled in the art will appreciate that the mechanisms of the invention are capable of being distributed in the form of computer program instructions in a variety of forms, which when executed on the data processing system, perform the methods described herein. The present invention applies regardless of the type of signal bearing medium used to carry out the distribution. Examples of signal bearing mediums include non-volatile hard-coded mediums, such as read-only memories; recordable type mediums such as floppy disks, hard disk drives, and CD-ROMs; and transmission type mediums such as digital and analog communication links.

While the invention has been particularly shown and described with reference to a preferred embodiment thereof, it will be understood by those skilled in the art that various other changes in form and detail may be made without departing from the spirit and scope of the invention.

What is claimed is:

1. A computer-implemented method for establishing a cardiovascular treatment therapy strategy for a patient, comprising the steps of:
    determining a cardiac risk classification group for the patient based on a predetermined set of cardiac risk factors;

determining a cardiovascular treatment therapy based on the patient's determined cardiac group risk classification and lipoprotein profile; and presenting the determined cardiovascular treatment therapy for the patient to a medical practitioner on a patient evaluation display.

2. The computer-implemented method for establishing a cardiovascular treatment therapy strategy of claim 1 wherein the predetermined set of cardiac risk factors comprises a first subset and a second subset of cardiac risk factors.

3. The computer-implemented method for establishing a cardiovascular treatment therapy strategy of claim 2 wherein the first subset of cardiac risk factors includes coronary heart disease, peripheral vascular disease, type II diabetes mellitus, an abdominal aortic aneurysm and symptomatic carotid disease.

4. The computer-implemented method for establishing a cardiovascular treatment therapy strategy of claim 2 wherein the second subset of cardiac risk factors includes a patient's age, a smoking status, a family history of cardiac disease, a diagnosis of systolic arterial hypertension and a systolic blood pressure treated condition.

5. The computer-implemented method for establishing a cardiovascular treatment therapy strategy of claim 1 wherein the step of determining a cardiac risk classification group comprises evaluation of the patient's medical history to determine if the patient has at least one medical condition in a first subset of cardiac risk factors.

6. The computer-implemented method for establishing a cardiovascular treatment therapy strategy of claim 5 wherein the step of determining a cardiac risk classification group further comprises determining a Framingham risk score for the patient.

7. The computer-implemented method for establishing a cardiovascular treatment therapy strategy of claim 5 wherein the step of determining a cardiac risk classification group further comprises evaluation of the patient's medical history to determine if the patient has at least two medical conditions in a second subset of cardiac risk factors.

8. The computer-implemented method for establishing a cardiovascular treatment therapy strategy of claim 5 wherein the patient is classified in a first risk classification group if the patient has at least one medical condition in a first subset of cardiac risk factors.

9. The computer-implemented method for establishing a cardiovascular treatment therapy strategy of claim 6 wherein the patient is classified in a first risk classification group if the patient has a Framingham risk score greater than 15.

10. The computer-implemented method for establishing a cardiovascular treatment therapy strategy of claim 7 wherein the patient is classified in a separate risk classification group if the patient has at least two medical conditions in the second subset of cardiac risk factors and has a Framingham risk score less than 12.

11. The computer-implemented method for establishing a cardiovascular treatment therapy strategy of claim 7 wherein the patient is classified in a separate risk classification group if the patient has at least two medical conditions in the second subset of cardiac risk factors and has a Framingham risk score of 12 or greater.

12. The computer-implemented method for establishing a cardiovascular treatment therapy strategy of claim 7 wherein the patient is classified in a separate risk classification group if the patient has less than two medical conditions in the second subset of cardiac risk factors.

13. The computer-implemented method for establishing a cardiovascular treatment therapy strategy of claim 5 wherein the first subset of cardiac risk factors includes coronary heart disease, peripheral vascular disease, type II diabetes mellitus, an abdominal aortic aneurysm and symptomatic carotid disease.

14. The computer-implemented method for establishing a cardiovascular treatment therapy strategy of claim 5 wherein the second subset of cardiac risk factors includes a patient's age, a smoking status, a family history of cardiac disease, a diagnosis of systolic arterial hypertension and a systolic blood pressure treated condition.

15. The computer-implemented method for establishing a cardiovascular treatment therapy strategy of claim 1 wherein the cardiac group risk classification group and cardiovascular treatment therapies are based on published medical guidelines and published medical literature.

16. The computer-implemented method for establishing a cardiovascular treatment therapy strategy of claim 15 wherein the published medical literature includes the effects of anti-lipid medicines on plasma concentration.

17. The computer-implemented method for establishing a cardiovascular treatment therapy strategy of claim 15 wherein the published medical literature includes the effects of anti-lipid medicines on composition of lipoprotein molecules and clinical outcomes.

18. The computer-implemented method for establishing a cardiovascular treatment therapy strategy of claim 1 further comprising presenting a medical guidelines recommendation for the patient to the medical practitioner on the patient evaluation display.

19. A computer program product for establishing a cardiovascular treatment therapy strategy, the computer program product comprising:

a recording medium;

program instructions recorded on the recording medium for determining a cardiac risk classification group for the patient based on a predetermined set of cardiac risk factors;

program instructions recorded on the recording medium for determining a cardiovascular treatment therapy based on the patient's cardiac group risk classification and lipoprotein profile; and program instructions recorded on the recording medium for presenting the determined cardiovascular treatment therapy for the patient to a medical practitioner on a patient evaluation display.

20. The computer program product for establishing a cardiovascular treatment therapy strategy of claim 19 wherein the program instructions for determining a cardiac risk classification group comprise program instructions for evaluation of the patient's medical history to determine if the patient has at least one medical condition in a first subset of cardiac risk factors.

21. The computer program product for establishing a cardiovascular treatment therapy strategy of claim 20 wherein program instructions for determining a cardiac risk classification group further comprise program instructions for determining a Framingham risk score for the patient.

22. The computer program product for establishing a cardiovascular treatment therapy strategy of claim 20 wherein the program instructions for determining a cardiac risk classification group further comprise program instructions for evaluation of the patient's medical history to determine if the patient has at least two medical conditions in a second subset of cardiac risk factors.

23. The computer program product for establishing a cardiovascular treatment therapy strategy of claim 20 further comprising program instructions for classifying the patient in a first risk classification group if the patient has at least one medical condition in a first subset of cardiac risk factors.

24. The computer program product for establishing a cardiovascular treatment therapy strategy of claim 21 further comprising program instructions for classifying the patient in a first risk classification group if the patient has a Framingham risk score greater than 15.

25. The computer program product for establishing a cardiovascular treatment therapy strategy of claim 22 further comprising program instructions for classifying the patient in a separate risk classification group if the patient has at least two medical conditions in the second subset of cardiac risk factors and has a Framingham risk score less than 12.

26. The computer program product for establishing a cardiovascular treatment therapy strategy of claim 22 further comprising program instructions for classifying the patient in a separate risk classification group if the patient has at least two medical conditions in the second subset of cardiac risk factors and has a Framingham risk score of 12 or greater.

27. The computer program product for establishing a cardiovascular treatment therapy strategy of claim 22 further comprising program instructions for classifying the patient in a separate risk classification group if the patient has less than two medical conditions in the second subset of cardiac risk factors.

28. The computer program product for establishing a cardiovascular treatment therapy strategy of claim 20 wherein the first subset of cardiac risk factors includes coronary heart disease, peripheral vascular disease, type II diabetes mellitus, an abdominal aortic aneurysm and symptomatic carotid disease.

29. The computer program product for establishing a cardiovascular treatment therapy strategy of claim 20 wherein the second subset of cardiac risk factors includes a patient's age, a smoking status, a family history of cardiac disease, a diagnosis of systolic arterial hypertension and a systolic blood pressure treated condition.

30. The computer program product for establishing a cardiovascular treatment therapy strategy of claim 19 wherein program instructions for determining the cardiac group risk classification group and program instructions for determining cardiovascular treatment therapies are based on published medical guidelines and published medical literature.

31. The computer program product for establishing a cardiovascular treatment therapy strategy of claim 30 wherein the published medical literature includes the effects of anti-lipid medicines on plasma concentration.

32. The computer program product for establishing a cardiovascular treatment therapy strategy of claim 30 wherein the published medical literature includes the effects of anti-lipid medicines on composition of lipoprotein molecules and clinical outcomes.

33. The computer program product for establishing a cardiovascular treatment therapy strategy of claim 19 further comprising presenting a medical guidelines recommendation for the patient to the medical practitioner on the patient evaluation display.

* * * * *